United States Patent [19]

Hoffman et al.

[11] Patent Number: 5,528,045

[45] Date of Patent: Jun. 18, 1996

[54] PARTICLE ANALYZER WITH SPATIALLY SPLIT WAVELENGTH FILTER

[75] Inventors: Robert A. Hoffman, Livermore; William J. Treytl, San Jose, both of Calif.

[73] Assignee: Becton Dickinson and Company, Franklin Lakes, N.J.

[21] Appl. No.: 417,743

[22] Filed: Apr. 6, 1995

[51] Int. Cl.$^6$ ............................ F21V 9/00; G01J 1/58; G21K 5/10; G01N 21/25

[52] U.S. Cl. ............................ 250/458.1; 250/459.1; 356/73; 356/418; 356/317; 356/318

[58] Field of Search ............................ 250/458.1, 462.1, 250/483.1, 484.2, 482.1, 485.1, 486.1, 487.1, 459.1; 356/418, 317, 318, 73

[56] References Cited

U.S. PATENT DOCUMENTS

| | | | |
|---|---|---|---|
| 4,243,318 | 1/1981 | Stöhr | 356/318 |
| 4,573,796 | 1/1986 | Martin et al. | 356/318 |
| 4,957,363 | 9/1990 | Takeda et al. | 356/73 |
| 5,270,548 | 12/1993 | Steinkamp | 250/458.1 |

OTHER PUBLICATIONS

John A. Steinkamp et al., "Three–Color Fluorescence Measurements on Single Cells Excited at Three Laser Wavelengths", *Cytometry* vol. 2, No. 4 (1982) pp. 226–229.

*Primary Examiner*—Constantine Hannaher
*Assistant Examiner*—Virgil O. Tyler
*Attorney, Agent, or Firm*—Allen W. Wark

[57] ABSTRACT

A fluorescence particle analyzer includes a flow tube through which particles marked with different fluorochromes pass from a first location to a second location. Emissions from the first and second locations are respectively imaged at respective first and second filter elements so that emissions that reach a photodetector from said first location are primarily filtered by the first filter element, while emission that reach the same photodetector from the second location are primarily filtered by the second filter element. The first filter element is selected to preferentially transmit emissions from a first fluorochrome at the expense of emissions from a second fluorochrome, while the second filter element is selected to preferentially transmit emissions from the second fluorochrome at the expense of emissions from the first fluorochrome. The first location is illuminated by a laser that preferentially excites the first fluorochrome at the expense of the second fluorochrome, while the second location is illuminated by a laser that preferentially excites the second fluorochrome at the expense of the first fluorochrome. The photodetector output includes a first pulse that corresponds predominately to the quantity of the first fluorochrome in the particle; subsequently, a second pulse appears corresponding predominantly to the quantity of the second fluorochrome in the particle. The use of the two filters minimizes cross talk between the fluorochrome emissions in the photodetector output pulses.

4 Claims, 1 Drawing Sheet

PARTICLE ANALYZER WITH SPATIALLY SPLIT WAVELENGTH FILTER

BACKGROUND OF THE INVENTION

The present invention relates to optical instruments and, more particularly, to instruments for distinguishing particles according to optical effects that occur when the particles pass illuminated locations. A major objective of the present invention is to provide for reduced fluorescence crosstalk in a multi-laser fluorescence analyzer.

Testing laboratories need to be able to detect the presence of certain entities, e.g., antigens, that can be difficult to detect directly. In some cases, the entities can be tagged with fluorochromes which are detectable. For example, the antibody for an antigen can be derivatized with a fluorochrome. The derivatized antibody can be mixed with a blood sample. To the extent an antigen is present in a cell, the derivatized antibody binds to it rendering it fluorescent. The tagged cells can be introduced into a cytometry system, wherein they can then be illuminated with monochromatic radiation, e.g., from a laser, that excites the fluorochrome. A photodetector can then detect the intensity of the fluorescent emissions.

It is often necessary to identify cells with a particular combination of antigens. To this end, several antibodies can be derivatized with respective fluorochromes; the derivatized antibodies are mixed with the blood sample under conditions sufficient for the antibodies to bind with the respective antigens. The cells are then illuminated and the resulting fluorescent emissions detected and measured.

To the extent possible, the fluorochromes are selected to have distinct emission spectra. A typical fluorescent analyzer can include a blue laser to excite fluorochromes that emit green, yellow, and red light, respectively. Dichroic mirrors or other wavelength-dispersive elements can split the emissions into green, yellow and red beams that are directed to respective photodetectors. In practice, it is difficult to distinguish more than three fluorochromes by wavelength alone due to overlap in emission spectra.

The number of distinguishable fluorochromes can be increased by using more than one excitation wavelength. This approach takes advantage of the fact that fluorochromes differ not only in their emission spectra, but in their excitation spectra. In an ideal case, two fluorochromes with nonoverlapping excitation spectra could be distinguished even where the emission spectra were identical. The distinction could be achieved by illuminating the fluorochromes at different times with two lasers, each selected to excite only a respective one of the fluorochromes. The resulting emissions would appear as two distinct signal pulses in the output of a single photodetector.

This approach is implemented in the context of a flow cytometry system by illuminating different locations along the flow tube with different laser wavelengths, each of which preferentially excites a respective fluorochrome. Tagged cells are made to flow past the two locations sufficiently infrequently that, usually, only one location is occupied at any given time. When a cell is at the first location, a photodetector pulse corresponds to the first fluorochrome; when later the cell is at a second location, a photodetector pulse corresponds to the second fluorochrome. Since the fluorochromes are distinguishable in the time domain, a single photodetector can be used to detect the emissions for both fluorochromes.

Cytometry systems in which a single photodetector is used to detect emissions resulting from spatially and wavelength separated excitations are disclosed or suggested by: 1) Donna J. Arndt-Jovin, Brian G. Grimwade, and Thomas M. Jovin, "A Dual Laser Flow Sorter Utilizing a CW Pumped Dye Laser" *Cytometry* Vol. 1, No. 2, 1980, pp. 127–131; 2) Eugene Hamori, Donna J. Arndt-Jovin, Brian G. Grimwade and Thomas M. Jovin, "Selection of Viable Cells with Known DNA Content" *Cytometry*, Vol. 1, No. 2, 1980, p. 132–1352; and 3) Julianne Meyne, Marty F. Bartholdi, Gayle Travis, and L. Scott Cram, "Counterstaining Human Chromosomes for Flow Karyology", *Cytometry*, No. 5, 1984, pp. 580–583.

In practice, each fluorochrome may be weakly excited by the excitation frequency that strongly excites the other fluorochrome. Thus, each fluorochrome can contribute "crosstalk" to the electrical pulse occurring in the time slot allotted to the other fluorochrome, resulting in erroneous readings. This crosstalk can be reduced by using two photodetectors, each positioned to receive only emissions from one of the excitation locations. However, this incurs the considerable expense and bulk associated with an additional photodetector. What is needed is a system that reduces crosstalk between fluorochromes that have substantially overlapping emission spectra and slightly overlapping excitation spectra without requiring an additional photodetector.

SUMMARY OF THE INVENTION

In accordance with the present invention, a particle analyzer includes a radiation source source for illuminating first and second illuminated locations, motion means for relatively moving a particle between the two locations, a photodetector for detecting changes in radiation when a particle passes by each of the illuminated locations, a split filter for altering the wavelength distribution of light bound for said photodetector, an optical subsystem for directing radiation from the two locations to the photodetector, and a signal analyzer for analyzing the output of the photodetector. "Radiation" herein refers to electromagnetic radiation.

In what follows, the invention is described primarily in the context of fluorescence analysis of particles in a flow cytometry system. It should be noted, however, that the invention also applies to scatter light detections, absorbance detections, etc. Furthermore, the present invention applies to scanning microscopes in which the illumination source is moved relative to stationary particles, as well as to flow cytometry systems which move particles relative to stationary light sources.

The split filter includes at least a first filter element that preferentially passes fluorescence from a first fluorochrome strongly excited by the first laser wavelength, while it relatively attenuates fluorescence from a second fluorochrome strongly excited by the second laser wavelength. The optical subsystem directs radiation from the first excitation location through the first filter to the photodetector, while it directs radiation from the second excitation location so that it reaches the photodetector without passing through the first filter element.

The split filter can include a second filter element to minimize the contribution of the first fluorochrome to the photodetector output pulse corresponding to the second fluorochrome. To this end, the optical subsystem directs relatively more of the fluorescence from the second location through the second filter element, and relatively less of the fluorescence from the first location through the second filter. This arrangement can be achieved by using optical elements that image the two excitation locations at the respective filter elements. A spatial filter can be disposed with apertures at or near the image plane to help isolate the images of the two locations. If there is no second filter element, the relative contributions of the two fluorochromes to fluorescence from the second location are not changed prior to detection.

While the separation of the emissions need not be perfect, more of the emissions passing from the first location to the photodetector should pass through the first filter element than not; likewise, more emissions passing from the second location to the photodetector should bypass the first filter element than pass through it. As a result, the attenuation of the second fluorochrome relative to the first fluorochrome in the emissions (filtered by the first filter element) from the first location to the photodetector should be greater than the attenuation of the second fluorochrome relative to the first fluorochrome in the emissions (which bypass the first filter element) from the second location to the photodetector.

The present invention can be applied to distinguish the four fluorochromes APC, PerCP, FITC, and RPE, where PerCP, FITC, and RPE are strongly excited by radiation having a wavelength about 488 nm, while APC is strongly excited by radiation having a wavelength about 635 nm. A single photodetector is used for detecting APC and PerCP. The filter elements of the split filter minimize cross talk between these fluorochromes. A five-way distinction can be achieved using the fluorochromes APC, PerCP, FITC, CUPE and BPE, by adding 532 nm excitation radiation that preferentially excites BPE. A split filter in front of the second photodetector reduces crosstalk between CUPE and BPE.

Prior art systems have provided for emissions generated by spatially separated excitation beams and detected by a single photodetector to be distinguished by time of detection. Each of the two fluorochromes to be detected by the single detector is strongly excited by a respective one of the laser beams and weakly excited by the other laser beam. However, the weak excitement results in cross talk in the photodetector output. A signal analyzer can compensate for this cross talk by digital and/or analog signal processing. However, there are limits to what post processing can achieve, and there is no substitute for beginning with pulses that are relatively free of crosstalk.

The present invention minimizes the cross talk by applying separate wavelength filters to the emissions from the two excitation locations. Thus, the invention distinguishes such emissions by both emission wavelength and time. This approach can reduce the need for post processing to speed analysis and/or provide better data to the signal processor to begin with so that its final results are more accurate.

The combination of time and wavelength discrimination of the fluorescence resulting from spatially separated excitations improves discrimination of the resulting signals by a single photodetector. The present invention provides improved rejection of secondary excitation where two or more fluorochromes with weakly overlapping excitation spectra are used, even with (moderately) overlapping emission spectra. This improved rejection is achieved economically without requiring an additional photodetector. Analysis of the photodetector output signal is unchanged except that less attention need be given to cross talk between the emissions from the two fluorochromes. These and other features and advantages of the present invention are apparent from the description below with reference to the following drawings.

DESCRIPTION OF THE PREFERRED EMBODIMENTS

Figure 1:
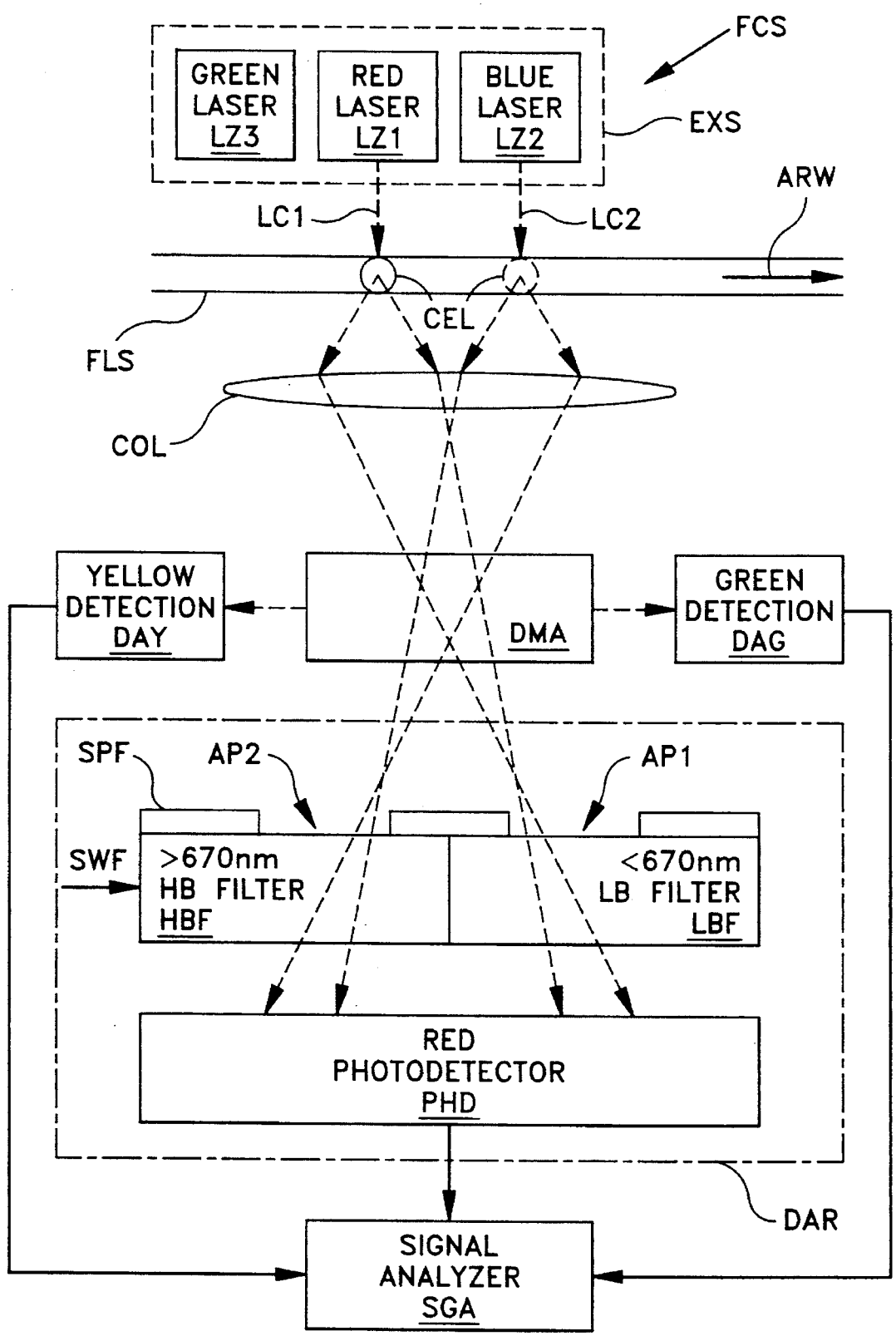
FIG. 1 is a schematic view of a flow cytometry system in accordance with the present invention.

In accordance with the present invention, a flow cytometry system FCS for characterizing a blood cell CEL comprises an excitation source EXS with lasers LZ1 and LZ2, a flow subsystem FLS, a collection lens COL, a dichroic mirror assembly DMA, three (red, yellow, green) detector assemblies DAR, DAY, and DAG, and a signal analyzer SGA, as shown in FIG. 1. Detector assembly DAR includes a spatial filter SPF with two apertures AP1 and AP2, a split wavelength filter SWF with a low-bandpass filter element LBF and a high bandpass filter element HBF, and a photodetector PHD. Detector assemblies DAY and DAG each include a spatial filter with one aperture and a photodetector. The three photodetectors have their outputs coupled to signal analyzer SGA.

A function of flow cytometry system FCS is to determine which, if any, of four antigens are carried by blood cells, including cell CEL. To this end, respective antibodies for the antigens are derivatized with respective fluorochromes allophycocyanin (APC), peridinin chlorophyl protein (PerCP). fluorescein isothiocyanate (FITC), and R-phycoerythrin (RPE). The blood cells are incubated with a mixture of these derivatized antibodies under conditions sufficient for antibodies to bind with their respective antigens to tag the blood cells. Unbound antibodies can be washed away. The tagged blood cells are then moved serially in a stream flowing past excitation locations LC1 and LC2.

To excite the fluorochrome-tagged cells, lasers LZ1 and LZ2 provide highly monochromatic light to respective excitation locations LC1 and LC2, which are about 120 microns apart. Laser LZ1 is a diode laser that provides red 635 nm radiation. Alternatively, red 633 nm radiation can be provided by a more expensive helium-neon laser for a more diffraction limited beam. Laser LZ2 is an argon ion laser that provides blue 488 nanometer (nm) radiation. Although shown otherwise for illustrative purposes, lasers LZ1 and LZ2 are preferably directed orthogonal to the direction along which emissions are detected to minimize noise in the detection signals.

When cell CEL reaches excitation location LC1 of flow subsystem FLS, the incident red excitation from laser LZ1 strongly excites any present APC fluorochrome; any present PerCP, RPE and FITC fluorochromes are at most weakly excited. When cell CEL reaches excitation location LC2, the incident blue excitation from laser LZ2 strongly excites any present PerCP, FITC, and RPE fluorochromes, and weakly excites any present APC fluorochrome.

The emissions are collected by collection lens COL and directed to dichroic mirror assembly DMA. Dichroic mirror assembly DMA basically includes two dichroic mirrors. The first transmits radiation below 560 nm to green detector assembly DAG and reflects radiation above 560 nm to the second dichroic mirror. The second dichroic mirror transmits radiation above 640 nm to red detector assembly DAR, and reflects radiation below 640 nm to yellow detector assembly DAY.

Accordingly, FITC fluorescence, which has an emissions peak at 520 nm is directed primarily from location LC2 to green detector assembly DAG; RPE fluorescence, which has an emissions peak at 570 nm, is directed primary from location LC2 to yellow detector assembly DAY; PerCP fluorescence, which has an emissions peak at 675 nm, is directed primarily from location LC2 to red detector assembly DAR; and APC fluorescence, which has an emissions peak at 660 nm, is directed primarily from location LC1 to red detector assembly DAR.

Collection lens COL is arranged to image cell CEL while it is at location LC1 within aperture AP1 so that the red (primarily APC) fluorescence from location LC1 is filtered by low-bandpass filter element LBF before impinging on photodetector PHD. Likewise, collection lens COL is arranged to image cell CEL while it is at location LC2 within aperture AP2 so that the red (primarily PerCP) fluorescence from location LC2 is filtered by high-bandpass filter HBF before impinging on photodetector PHD. Collection lens COL provides about 14×magnification so that the centers of apertures AP1 and AP2 are 1.7 millimeters (mm) apart. The widths of apertures AP1 and AP2 are 1.0

Low-bandpass filter element LBF has a high cut off of about 670, near the crossover for the APC and PerCP emission spectra. Accordingly, PerCP emissions from location LC1 are attenuated relative to APC emissions from location LC1. Low-bandpass filter LBF has a low cut off of about 650 nm, to exclude stray excitation from red laser LZ1.

High-bandpass filter element HBF has a low cut off of about 670 nm, at about the cross over for the APC and PerCP emission spectra. Thus, APC emissions from location LC2 are attenuated relative to PerCP emissions from location LC2. High bandpass filter element HBF has a high cut off of about 700 nm, to minimize background noise at wavelengths longer than those within the emission spectrum PerCP. In practice, noise in this range is weak, so a high-pass filter can be used in place of high-bandpass filter element HBF.

Thus, when cell CEL is at excitation location LC1, any APC fluorescence is sensitively detected by red detector assembly DAR, while any PerCP crosstalk is reduced by low-bandpass filter element LBF. When cell CEL is at excitation location LC2, any PerCP fluorescence is strongly detected by red detector assembly DAR, while any APC crosstalk is reduced by high-bandpass filter element HBF. Any FITC or RPE emissions are detected respectively by photodetector assemblies DAG and DAY.

Signal analyzer SGA analyzes the outputs of detector assemblies DAR, DAY, and DAG to identify and quantify fluorochromes in passing cells, such as cell CEL. Flow cytometry system FCS includes scatter detectors at location LC1 that detect the presence of a cell, irrespective of its fluorescence. This detection can be used by signal analyzer SGA as a reference to time detected pulses to distinguish pulses resulting from excitation at the different excitation locations. (In addition, the scatter pulses can be analyzed to determine size and granularity.) Optionally, the pulses can be corrected as in the prior art, but to a lesser extent, to compensate for fluorochrome crosstalk not eliminated by split filter SPW.

The foregoing description relates to a four-way discrimination among fluorochromes. Five-way discrimination can also be implemented with the following modifications. A third laser LZ3, located upstream of first laser LZ1 is used to provide green 532 nm excitation to a third excitation location along flow subsystem FLS; laser LZ3 is a frequency doubled neodymium-yttrium-aluminum-garnet (NdYAG) laser. The five fluorochromes are FITC, CU-phycoerythrin (CUPE), B-phycoerythrin (BPE), APC, and PerCP. BPE is strongly excited by green laser LZ3; while CUPE, like RPE, is strongly excited by blue laser LZ2. A second split filter is disposed in front of green detector assembly DAG to reduce mutual crosstalk between CUPE and BPE. A dual-aperture spatial filter replaces the single aperture spatial filter in front of detector assembly PDG.

Collection lens COL respectively images first excitation location LC1 and the third excitation location within these apertures. Thus, yellow, predominantly BPE emissions from the third excitation location are transmitted through a low-bandpass filter element, while yellow, predominantly CUPE emissions from second excitation location LC2, are transmitted through a high-bandpass filter. The low-bandpass filter has a range from 540, to attenuate green excitation radiation, to 565, to attenuate BPE in favor of CUPE. The high-bandpass filter has a range from 565, to attenuate CUPE in favor of BPE, to 620, to filter out ambient excitation radiation from red laser LZ1. Thus, mutual BPE/CUPE crosstalk is reduced in the same manner as mutual APC/PerCP crosstalk.

Flow cytometry system FCS can be used, not only to detect antigens, but any fluorescent particles, including other ligands having fluorochrome derivatized ligand binders attached. The references cited in the background section above give examples of alternative fluorescent particles.

In the preferred embodiment of the invention, dichroic mirrors separate beams by wavelength. Alternative embodiments dispense with the dichroic mirrors, relying on the split filter elements and other bandpass filters to reject emissions not intended for the respective photodetector.

The number of fluorochromes that can be distinguished by the present invention can be augmented in a variety of ways. More 0 photodetectors can be used, in principle, to distinguish more fluorochromes with only weakly overlapping emissions. More filter elements per split filter (and more apertures per spatial filter) can be used to distinguish more fluorochromes per photodetector where at least an equal number of excitation sources of like or different excitation wavelengths are used. For example, FITC, BPE, and APC can be excited by three (blue, green, red) lasers and detected with a single photodetector with a three-way split filter. Similarly, FITC, RPE and PerCP can be excited by three blue lasers. Furthermore, a greater percentage of photodetectors can be used to detect multiple fluorochromes. Greater resolution of fluorochromes can be achieved by correlating photodetector outputs.

The invention provides for the split filter having only one split filter element, e.g., LBF. The split filter slot occupied in the preferred embodiment by high-bandpass filter element HBF can instead be left empty or filled with clear glass. In this case, PerCP is transmitted to the relative exclusion of APC, but the converse advantage is not attained. Nonetheless, the single-element split filter provides an advantage over the prior art with some cost saving relative to the preferred embodiments.

Instead of bulk filter elements, fiber optics can be used to direct emissions between excitation locations and photodetectors. By filtering emissions before entrance to the fibers, or by filtering using narrow bandwith fibers, the invention can be practiced using a single photodetector for any number of fluorochromes.

While the preferred embodiment used multiple lasers to produce different excitation wavelengths, other embodiments use a single laser with beam splitting to excite different location. Frequency shifting devices permit different excitation wavelengths. Alternatively, two excitation locations can be excited by the same wavelength. While the excitation and fluorescence detection are orthogonal in the preferred embodiment, the present invention provides for "epi" configurations in which they are not orthogonal. The excitation source need not be a laser; a flashlamp, arc lamp or an incandescent lamp can be used with proper spatial and wavelength filtering to provide the desired excitation and multiple excitation locations.

Instead of reducing crosstalk between fluorochromes, the present invention can be used to reduce crosstalk between scattered light detectors at two locations. One filter element can preferentially pass wavelengths associated with illumination at the first location, while the other filter element can preferentially pass wavelengths associated with illumination at the second location. Alternatively, one filter element can be tuned for scatter detection while the other is tuned for fluorescence.

Visible excitation and emission are used in the preferred embodiment. However, invention provides for the use of both longer and shorter electromagnetic radiation for either or both of the excitation radiation and the emission radiation.

In the context of a flow cytometry system, blood cells are made to pass through stationary laser beams. In the context of a scanning microscope, the laser beams can be moved relative to stationary fluorescent particles. These and other modifications to and variations upon the preferred embodiments are provided for by the present invention, the scope of which is limited only by the following claims.

What is claimed is:

1. A particle analyzer comprising:
   an excitation source for illuminating a first location and a second location;
   motion means for relatively moving a particle between said first location and said second location;
   a photodetector for making detections of changes in radiation from said first location and said second location when said particle is in one of those locations, said photodetector having an output for outputting pulses in response to said detections;
   signal analyzer means for analyzing said pulses;
   filter means for altering the wavelength distribution of said radiation, said filter means including a first filter element that attenuates fluorescent intensity at a first wavelength more than at a second wavelength; and
   optical path means directing said radiation to said photodetector means from said first location and said second location so that
   most of the radiation directed from said first location to said photodetector passes through said first filter element, and
   most of the radiation directed from said second location to said photodetector bypasses said first filter element;
   whereby, the ratio of attenuation of said first wavelength to the attenuation of said second wavelength is greater for radiation directed from said first location to said photodetector than it is for radiation directed from said second location to said photodetector.

2. A system as recited in claim 1 wherein said filter means includes a second filter element that attenuates radiation at said second wavelength more than radiation at said first wavelength, said optical path means directing said radiation so that most of the radiation directed from said second location to said photodetector passes through said second filter element.

3. A system as recited in claim 2 wherein said optical path means images said first location at said first filter element and images said second location at said second filter element.

4. An analytical system capable of distinguishing between two fluorochromes, a first of said fluorochromes having a first excitation spectrum with a first peak excitation wavelength and a first emission spectrum with a first peak emission wavelength, a second of fluorochromes having a second excitation spectrum with a second peak excitation wavelength and a second emission spectrum with a second peak emission wavelength, said first and second excitation spectrums overlapping, said first and second emission spectrums overlapping, said first peak emission wavelength differing from said second peak emission wavelength, said system comprising:
   first laser means for illuminating a first location with light having a first laser wavelength within said first and second excitation spectra, but closer to said first peak excitation wavelength than to said second peak excitation wavelength;
   second laser means for illuminating a second location with light having a second laser wavelength within said first and second excitation spectra, but closer to said second peak excitation wavelength than to said first peak excitation wavelength;
   motion means for relatively moving a particle including one of said materials between a first location and a second location;
   a photodetector for detecting light within a detection wavelength range that includes both of said peak emission wavelengths, said photodetector means having an output for outputting an electrical signal having a magnitude that varies as a function of the intensity of light detected by said photodetector;
   filter means for altering the wavelength distribution of incident radiation, said filter means including a first filter element that attenuates light intensity at said first peak emission wavelength more than at said second peak emission wavelength, said filter means including a second filter element that diminishes radiation at said second peak emission wavelength more than radiation at said first peak emission wavelength;
   optical path means for directing emissions from said first and second locations so that most of the emissions directed from said first location to said photodetector pass through said first filter element and so that most of the emissions directed from said second location to said photodetector pass through said second filter element; and
   signal analyzer means for analyzing said electrical signal.

* * * * *